United States Patent
Andreas

(10) Patent No.: US 7,583,784 B2
(45) Date of Patent: Sep. 1, 2009

(54) METHOD FOR CALCULATING COMPUTED TOMOGRAPHY PICTURES FROM DETECTOR DATA OF A CT HAVING AT LEAST TWO RADIATION SOURCES

(75) Inventor: Lutz Andreas, Poxdorf (DE)

(73) Assignee: Siemens Aktiengesellscahft, Munich (DE)

( * ) Notice: Subject to any disclaimer, the term of this patent is extended or adjusted under 35 U.S.C. 154(b) by 0 days.

(21) Appl. No.: 11/499,667

(22) Filed: Aug. 7, 2006

(65) Prior Publication Data
US 2007/0098136 A1    May 3, 2007

(30) Foreign Application Priority Data
Aug. 8, 2005    (DE) ................... 10 2005 037 368

(51) Int. Cl.
*A61B 6/00* (2006.01)
(52) U.S. Cl. ................ 378/9; 378/4; 378/92; 378/901
(58) Field of Classification Search ............... 378/4, 378/9, 92, 95, 901
See application file for complete search history.

(56) References Cited

U.S. PATENT DOCUMENTS

| | | | | |
|---|---|---|---|---|
| 5,375,156 A * | 12/1994 | Kuo-Petravic et al. | ......... | 378/9 |
| 5,400,255 A * | 3/1995 | Hu | ................ | 378/4 |
| 5,473,654 A * | 12/1995 | Kotian et al. | ................ | 378/4 |
| 5,533,080 A * | 7/1996 | Pelc | ................ | 378/5 |
| 5,740,224 A * | 4/1998 | Muller et al. | ................ | 378/11 |
| 5,966,422 A * | 10/1999 | Dafni et al. | ................ | 378/9 |
| 6,198,790 B1 * | 3/2001 | Pflaum | ................ | 378/9 |
| 6,421,412 B1 * | 7/2002 | Hsieh et al. | ................ | 378/9 |
| 6,810,102 B2 * | 10/2004 | Hsieh et al. | ................ | 378/4 |
| 6,845,141 B2 * | 1/2005 | Flohr et al. | ................ | 378/4 |
| 6,856,666 B2 * | 2/2005 | Lonn et al. | ................ | 378/8 |
| 7,016,455 B2 * | 3/2006 | Bruder et al. | ................ | 378/9 |
| 7,039,152 B2 * | 5/2006 | Bruder et al. | ................ | 378/8 |
| 2002/0085664 A1 * | 7/2002 | Bromberg et al. | ............. | 378/4 |
| 2003/0128801 A1 * | 7/2003 | Eisenberg et al. | ............. | 378/19 |

(Continued)

FOREIGN PATENT DOCUMENTS

| | | |
|---|---|---|
| DE | 103 02 565 A1 | 8/2004 |
| DE | 103 54 900 A1 | 6/2005 |
| WO | WO 2004080310 A1 * | 9/2004 |

OTHER PUBLICATIONS

Feldkamp et al., Practical Cone-Beam Algorithm, Optical Society of America, vol. 1, No. 6, Jun. 1984, pp. 612-619.*

(Continued)

*Primary Examiner*—Edward J Glick
*Assistant Examiner*—Alexander Tanignco
(74) *Attorney, Agent, or Firm*—Harness, Dickey & Pierce, P.L.C.

(57) ABSTRACT

A method is for calculating computed tomography pictures from detector data of a CT that uses at least two radiation sources that generate different conical beams. A spatial distribution of attenuation values of a scanned object is reconstructed with the aid of detector data of a first relatively large conical beam. The integral attenuation values that are required to supplement the relatively small conical beam are back calculated from the previously reconstructed data. Finally, a reconstruction of computed tomography pictures is subsequently carried out with the aid of the back calculated integral attenuation data and the measured integral attenuation data of the relatively small conical beam.

21 Claims, 4 Drawing Sheets

U.S. PATENT DOCUMENTS

| | | | | |
|---|---|---|---|---|
| 2004/0114710 A1* | 6/2004 | Ozaki | | 378/9 |
| 2004/0247070 A1* | 12/2004 | Ali et al. | | 378/4 |
| 2005/0111623 A1* | 5/2005 | Bruder et al. | | 378/95 |
| 2006/0111623 A1* | 5/2006 | Stetson | | 600/336 |
| 2006/0193430 A1* | 8/2006 | Kuhn | | 378/9 |

OTHER PUBLICATIONS

Crawford et al., Computed Tomography Scanning with Simultaneous Patient Translation, Med. Phys., 17, 6, Nov./Dec. 1990, pp. 967-982.*

* cited by examiner

METHOD FOR CALCULATING COMPUTED TOMOGRAPHY PICTURES FROM DETECTOR DATA OF A CT HAVING AT LEAST TWO RADIATION SOURCES

PRIORITY STATEMENT

The present application hereby claims priority under 35 U.S.C. §119 on German patent application number DE 10 2005 037 368.2 filed Aug. 8, 2005, the entire contents of which are hereby incorporated herein by reference.

FIELD

The invention generally relates to a method for calculating computed tomography pictures. For example, it may be directed to a method for calculating computed tomography pictures from detector data of a CT that has at least two radiation sources that generate conical beams that are equipped with fan angles of different size and scan an object in a circular or spiral fashion.

BACKGROUND

Methods and the computed tomography apparatuses associated therewith are generally known, such computed tomography systems in use mostly being in this case systems having a number of tube/detector arrangements, the readings of a detector system that does not cover the entire measuring field width being supplemented by the edge channels of another detector system, which covers the entire measuring field, in order to reconstruct the computed tomography pictures. In this case, the edge channels are taken from readings which are such that have taken measurements that are as close as possible in time to the same gantry/angular and focal position. Such a supplement is carried out in this case from scratch with each reconstruction.

Various disadvantages can occur when carrying out such a resolution. Thus, it is possible, for example, in the case of a measurement with continuous table advance, that is to say during spiral operation, that the two measurement systems are not at the same point with reference to the system axis when its angular position corresponds, and so the same measurement positions come to be applied here only approximately.

It is also possible for the signal-to-noise ratio of the channel data of readings of the two systems at the same angle and at the same position to differ clearly in the case of a measurement in which a dosage modulation known per se is undertaken, the result being that their comparability and exchangeability are not necessarily given.

Furthermore, it can be that measured values that are required to supplement one system are not present in the other system in the case of temporary triggered partial revolution measurements such as is the case, for example, with cardio pictures.

Another problem arises when the scanning systems used are operated at different tube voltages or with different energy spectra, the result being, on the basis of the energy dependence of the absorption constants of the X-rayed tissue that the measured attenuation values of the scans can no longer be compared with one another straight away. Thus, in the case of a simple supplementing of measured data by the respective other system, errors can occur that are based on the different energy spectra of the radiation of the scanning system that is used.

SUMMARY

A method, in at least one embodiment, is provided for calculating computed tomography pictures from detector data of a CT having at least two radiation sources that lessens and/or does not exhibit at least one of the above-named problems.

The inventor has realized, in at least one embodiment, that in the case of a computed tomography system that uses a number of conical beams of different size, it can be more advantageous to use the data of the relatively large conical beam firstly to carry out a reconstruction, to calculate the spatially distributed attenuation values of the scanned object, and to use these in turn, vice versa, to determine the integral attenuation values required for supplementing the relatively small conical beams. It is thereby possible for the detector data of the relatively small system to be supplemented at the edge and to carry out a reconstruction with the supplemented data with convolution and back projection.

This basically corresponds to a virtual expansion of the channels of the relatively small detector, use being made for this purpose of a previously reconstructed tomogram, or of volume data of the object in order to calculate the absorption of virtual beams that would strike the expanded, relatively small detector. In the case of such an expansion of the channel data, transitional areas between the actually measured and virtual channels can be adapted to one another by an appropriate transitional filtering such that no jumps can occur and be able to lead to artifacts in the image calculation.

It is also possible by way of such a method, in at least one embodiment, to carry out an appropriate adaptation of the virtually calculated absorption data when use is made of different acceleration voltages, such that no artifacts are thereby produced in the reconstruction of the data of the relatively small conical beam.

In accordance with at least one embodiment of the invention, the inventor proposes a method for calculating computed tomography pictures from detector data of a CT that has at least two radiation sources that generate conical beams, at least two conical beams having fan angles of different size and measuring fields of different size scanning an object in a circular or spiral fashion, and integral attenuation values being measured. In this case, spatial attenuation values of the object are reconstructed by convolution and back projection with the aid of at least one first relatively large conical beam that completely surrounds the object, and the object likewise is scanned with the aid of at least one second relatively small conical beam, the measuring field of the second conical beam not completely surrounding the object. The integral attenuation of virtual rays cutting this area is calculated from the calculated spatial attenuation values outside the measuring field of the relatively small second conical beam, and the measured integral attenuation values of the second relatively small conical beam are supplemented at the edge with the aid of these virtual integral attenuation values calculated, the spatial attenuation values of the object being reconstructed at least in the relatively small measuring field on the integral attenuation values thus supplemented.

It is advantageous when seen in the direction of rotation of the conical beam if the at least one relatively large conical beam scans the object upstream of the at least one relatively small conical beam, since a reconstruction of the relatively large measuring field can already be to hand thereby in advance of the completion of the scanning of the small conical beam.

As already mentioned above, it is further advantageous when transitional filtering is carried out in the transitional area between the virtual integral attenuation values and the measured integral attenuation values of the relatively small conical beam. Moreover, a normalization can be carried out with the aid of the virtual integral attenuation values and the measured integral attenuation values of the relatively small conical beam.

This normalization compensates measuring errors that are caused, for example, by oblique collimator states or the plate offset of the tube anode. In general, it is assumed with such normalizations that no object is X-rayed at the edge of a measuring field, and that therefore no attenuation occurs. This can be checked, for example, by setting threshold values.

The profiles of all the rows of a reading can be corrected in this case such that they no longer exhibit any attenuation at the edge of the measuring field. In the case of at least one embodiment of the method used here, in which a normalization must be undertaken with a reduced measuring field, it is to be assumed that even the outer channels are attenuated by the object and that therefore normalization cannot be carried out in the known way. However, it is possible to compare a compensation of the theoretical attenuation profiles, which can be gathered from the previously reconstructed image, with the actually measured profiles of the small conical beam, and thereby to carry a normalization.

It is also possible for the conical beams used to have different energy spectra, and for this difference to be taken into account when calculating the virtual integral attenuation values. It is possible thereby, for example, to use the HU values calculated with the aid of the first conical beam to determine the respective tissue at this point and, in accordance with the knowledge of the variation in the attenuation behavior with reference to the different energy spectra, to deduce the actual attenuation values by using the energy spectrum of the relatively small conical beam, and to determine the corresponding virtual integral attenuation value of the beam being sought.

The method described, in at least one embodiment, can be used both in conjunction with single row detectors and in conjunction with multirow detectors.

Further variants exist in that in the case of a circular scan all the conical beams run in a common slice layer or, to express it more simply, are arranged on a common slice plane, or a spiral scan can take place and all the starting points of the conical beams can be arranged with regard to the respectively selected advance such that they run on a common spiral.

However, it is also possible in principle for a spiral scan to take place, the starting points of the conical beams advantageously being arranged on a common slice plane perpendicular to the system axis. This corresponds to the usual design of multifocal/multidetector systems in the case of which the focuses and detectors are arranged on a common gantry and move on the same circular track—without reference to the patient, who may be moving along the system axis. It is pointed out in this context that the described reconstruction methods, and also the reverse virtual back calculation of radiation attenuations on the basis of existing spatial attenuation values in the object make use of approximation methods with the aid of which the respective exactly desired beam is interpolated from known adjacent beams or data. Likewise, attenuation values are determined at a specific prescribed location by interpolations of known attenuation values in the neighborhood of the respectively defined coordinate.

Furthermore, it is within the scope of at least one embodiment of the invention when different reconstruction methods are carried out with the aid of the attenuation data of the relatively large conical beam and of the at least one relatively small conical beam. Thus, for example, a 3D reconstruction method, preferably a voxelwise reconstruction, is carried out with the aid of the attenuation data of the at least one relatively small conical beam while a 2D reconstruction method is carried out with the aid of the attenuation data of the at least one relatively large conical beam.

It is likewise possible, for example, that a cardio reconstruction, preferably making use of simultaneously determined ECG data, is carried out with the aid of the attenuation data of the at least second or else third relatively small conical beam while the relatively large conical beam is used to generate a normal recording that is not time triggered or heart phase triggered. Since no substantial change takes place in a peripheral area owing to the movement of the heart, it is possible here to operate with a simple method, if appropriate also with a reduced radiation dose, while use is made of a method that is more complicated and more detailed or more high time resolved in the area of the small measuring field that surrounds the heart region, for example.

Thus, it is thereby possible overall to adapt the reconstruction method individually to the requirements of the scanned area, and an appropriate adaptation to the different reconstruction methods can be performed by way of the reconstruction performed in the meantime, and subsequently determining attenuation data of virtual beams in order to supplement the relatively small conical beam.

The method described here is suitable both for the use of CT systems in the case of which each individual focus is assigned a dedicated detector, or it is also possible to apply this method to CT systems in the case of which use is made of a single stationary detector that comprises 360° and has a number of rotating foci or radiation sources.

A particular variant, preferred in practice by the inventor, of at least one embodiment of the inventive method provides that seen in the direction of rotation of the conical beam, the relatively large conical beam scans the object upstream of the at least relatively small conical beam, that, furthermore, tomograms are reconstructed from the measured data of the large measuring field, and a three-dimensional image stack is produced. Subsequently, this image stack is used to calculate the integral virtual attenuation values for the measurement positions of the relatively small measuring field, the virtual attenuation values being determined for the large measuring field. This particular variant can also fundamentally be combined with other method steps named above and not contradictory per se.

It is also to be noted without restriction on the generality of at least one embodiment of the invention that in the case of a multidetector CT system, it is in practice currently mostly similar reconstruction methods that are applied for the measurement systems, and associated images of the two measurement systems are overlaid in an additional reconstruction step and processed to form a common image. As a rule, if the selected image section is of appropriate size, the image information of the large measurment system is used in the outer measuring area that has been acquired only by the large measuring field. Of course, a critical concern here is the transitional area that is susceptible to image artifacts if the two measurement systems have sharply deviating image information.

Also within the scope of at least one embodiment of the invention is a computed tomography system having at least two radiation sources that scan an object with the aid of conical beams with different widths, the attenuation of the radiation on passage through the object being determined, and tomograms or volume data of the spatial attenuation of the object being determined therefrom with the aid of a central processor and programs or program modules stored therein, there being inventively included in the programs or program modules program code that simulates the previously described method steps during operation.

BRIEF DESCRIPTION OF THE DRAWINGS

The invention is described in more detail below with reference to the example embodiments and with the aid of the figures, only the features required to understand the invention being illustrated, and the following reference symbols being used: 1: CT system; 2: X-ray tube; 3: small detector; 4: X-ray tube; 5: large detector; 6: gantry housing; 7: patient; 8: moveable patient couch; 9: system axis; 10: arithmetic logic and control unit; 11: small conical beam; 12: small measuring field; 13: large conical beam; 14: large measuring field; 101 to 108: method steps; 201 to 207: method steps; $F_A$: first focus; $F_B$: second focus; $D_A$: detector row of the large detector; $D_B$: detector row of the small detector; $Prg_1$ to $Prg_n$: computer programs.

In detail.

DETAILED DESCRIPTION OF THE EXAMPLE EMBODIMENTS

Figure 1:
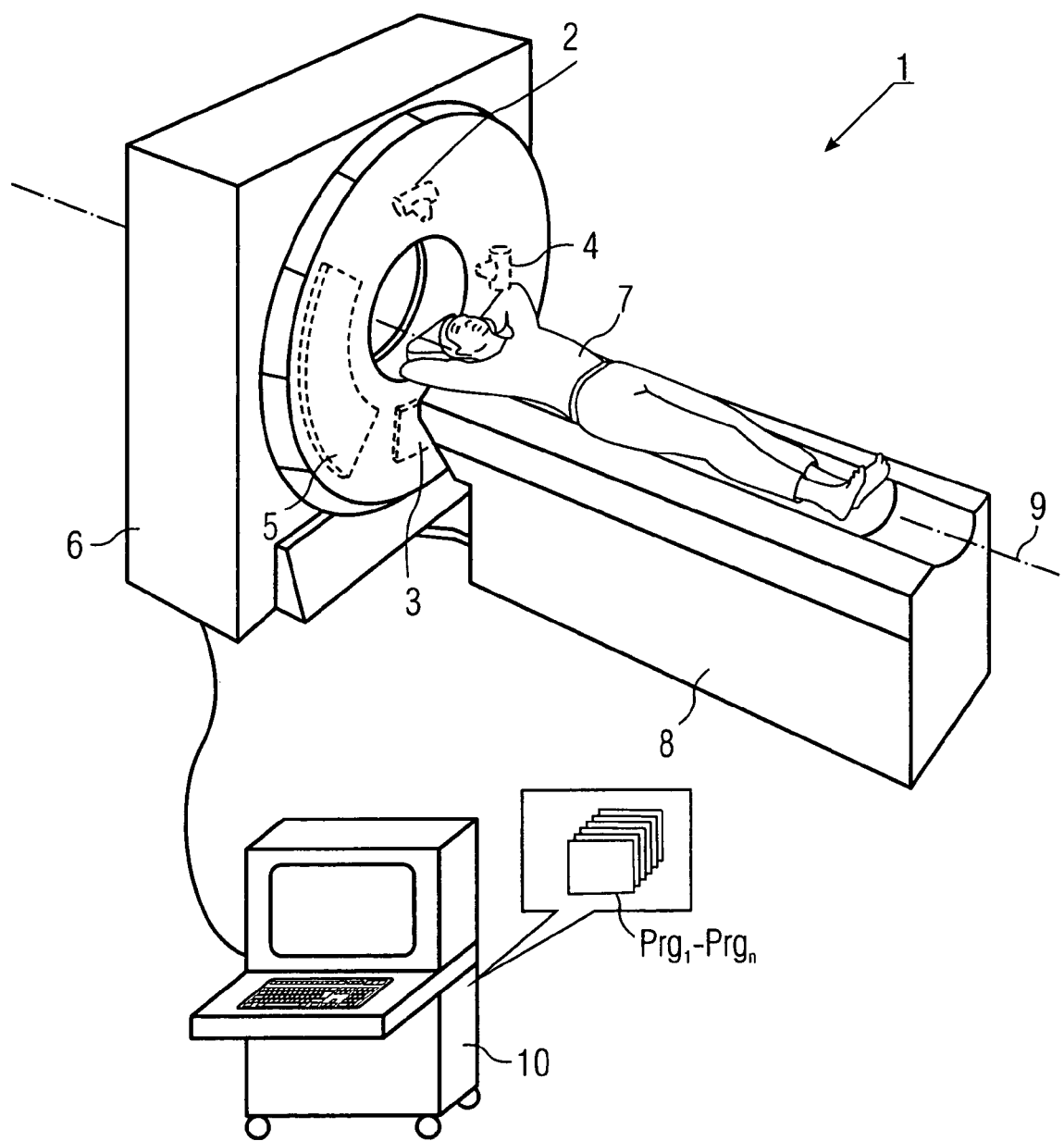
FIG. 1 shows a 3D schematic of a computed tomography system having two tube/detector systems.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows by way of example a computed tomography system 1 that has two X-ray tubes 2 and 4 that are offset by 90° and have oppositely situated detectors 3 and 5 that are arranged in a gantry housing 6 and each generate conical beams—not illustrated here—for scanning a patient 7 and measuring the attenuation thereof on the respectively oppositely situated detector. The patient 7 is located on a displaceable patient couch 8 and is guided during the examination between the X-ray tubes 2, 4 and the oppositely situated detectors 3, 5, and scanned in the process. The attenuation of the X-radiation caused by the patient during scanning is recorded with the aid of the detectors 3, 5, and the detector output data thus determined are passed on via a line to the arithmetic logic and control unit 10 where computer programs $Prg_1$ to $Prg_n$ are used in a way according to at least one embodiment of the invention to reconstruct CT representations.

It remains to be mentioned that the arithmetic logic and control unit 10 also executes the actual control of the computed tomography system 1 and can also control the displacement of the patient 7 along the system axis 9 through the gantry. Lines that may possibly be required for recording ECG currents if a cardio reconstruction is carried out are not illustrated in the present FIG. 1.

Figure 2:
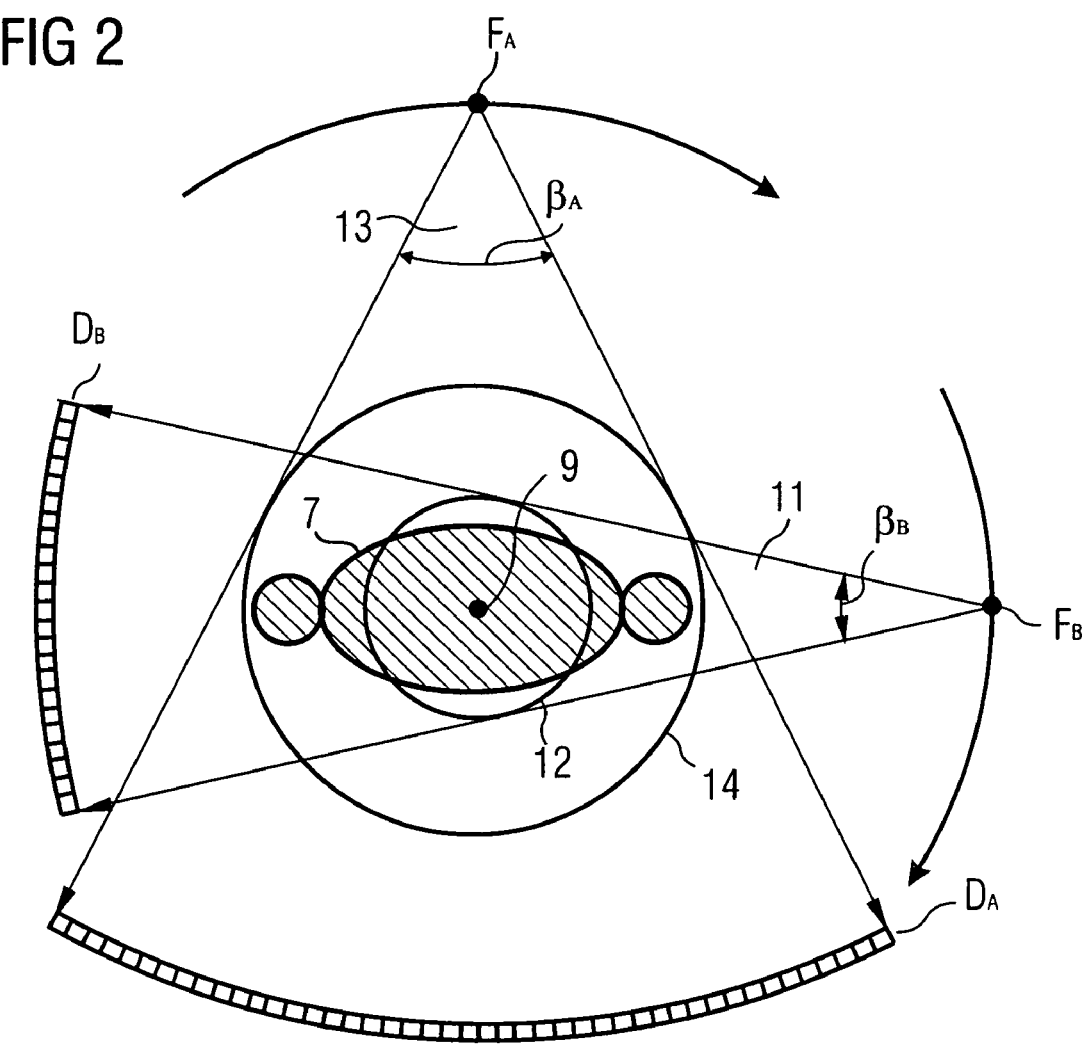
FIG. 2 shows a cross section through a two tube/detector system having conical beams of different fan angles.

FIG. 2 is a schematic of a section perpendicular to the system axis 9 in the region of the tube/detector arrangement. The first step is to image a focus $F_A$ starting from which a relatively wide conical beam 13 having a fan angle of $\beta_A$, which scans a measuring field 14, strikes an oppositely situated detector row $D_A$. Offset by approximately 90° thereto is to be seen a further focus $F_B$ from which a relatively small conical beam 11 having a fan angle $\beta_B$ emanates, strikes a detector row $D_B$ of the detector 3 and includes a relatively small measuring field 12. The patient 7 likewise depicted in the section certainly on the one hand is unambiguously situated in the large measuring field 14, but parts of the patient 7 are arranged outside the measuring field 12 such that rays of the focus/detector combination of the conical beam 11 are subjected outside the measuring field 12 to absorptions that cannot be detected by way of these conical beams alone.

According to at least one embodiment of the invention, in order to generate this information that is initially not present, the large conical beam 13 is used to reconstruct an image with the spatial attenuation data of the patient. Starting from these reconstructed data, the edge regions not acquired in the small conical beam 11 are calculated with reference to their absorption to be expected, and the additional information in the edge region is supplemented for the actual reconstruction of the image from the detector data of the relatively small detector or of the relatively small conical beam 11 by such virtually determined attenuation data.

The reconstruction is then carried out from the actually measured detector data and the virtual, back calculated detector data. It is possible thereby for the two conical beams, if appropriate also a number of conical beams, to operate with the aid of the corresponding focus/detector systems in a fashion largely decoupled from one another. Thus, for example, an adaptation of the dose power of the two radiation sources can be performed independently of one another, for example an adaptation of the dose power in small conical beams corresponding to a continuous ECG measurement, while the large conical beam operates independently thereof, or different X-ray spectra can be used in two or more conical beams.

Figure 3:
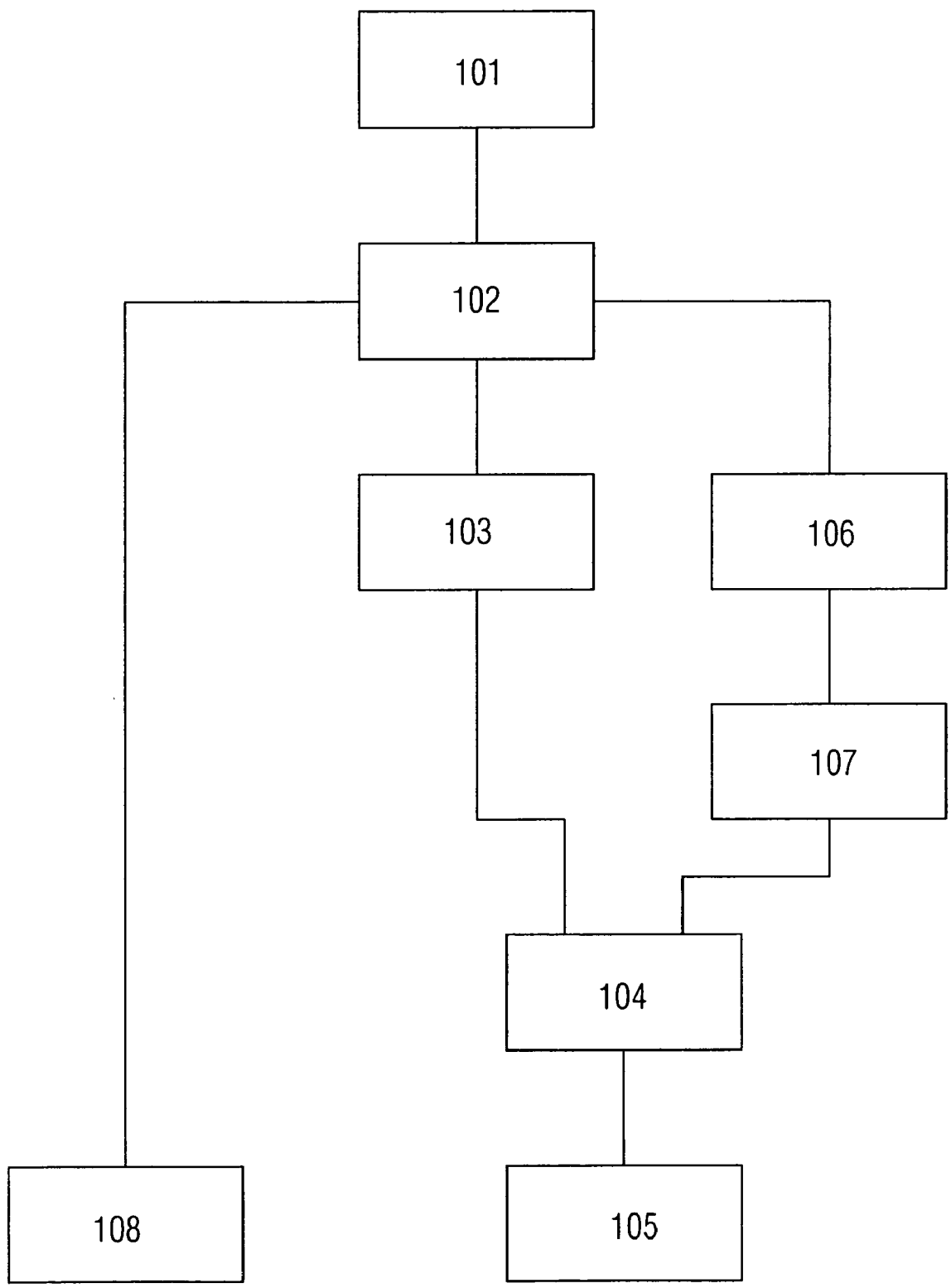
FIG. 3 shows a method scheme according to an embodiment of the invention.

FIG. 3 illustrates an exemplary method scheme for carrying out the method according to at least one embodiment of the invention. In accordance therewith, a measurement is carried out in step 101 with the aid of two detector systems having a large and small conical beam. In step 102, the measured data of the two detector systems are preprocessed, and the measured data of the relatively large detector system are stored in step 108.

In step 103, the measured data of the relatively small detector system having a relatively small measuring field are stored, while carried out in parallel thereto in step 106 from the data of the relatively large detector system is a reconstruction of, for example, an image stack. This is done with the aid of a subsequent back calculation of the attenuation values 107 that must be supplemented to form the relatively small measuring field. The supplementation of the measured data of the relatively small measuring field with the back calculated virtual data takes place in step 104, an additional normalization of these data taking place, as outlined above, and the entire data subsequently being stored in step 105.

Subsequently, a reconstruction can be carried out both with the aid of the directly measured raw data of the relatively large measuring field, and with the aid of the virtually supplemented raw data of the relatively small measuring field, it not necessarily being imperative to use an identical reconstruction method for both data records.

Figure 4:
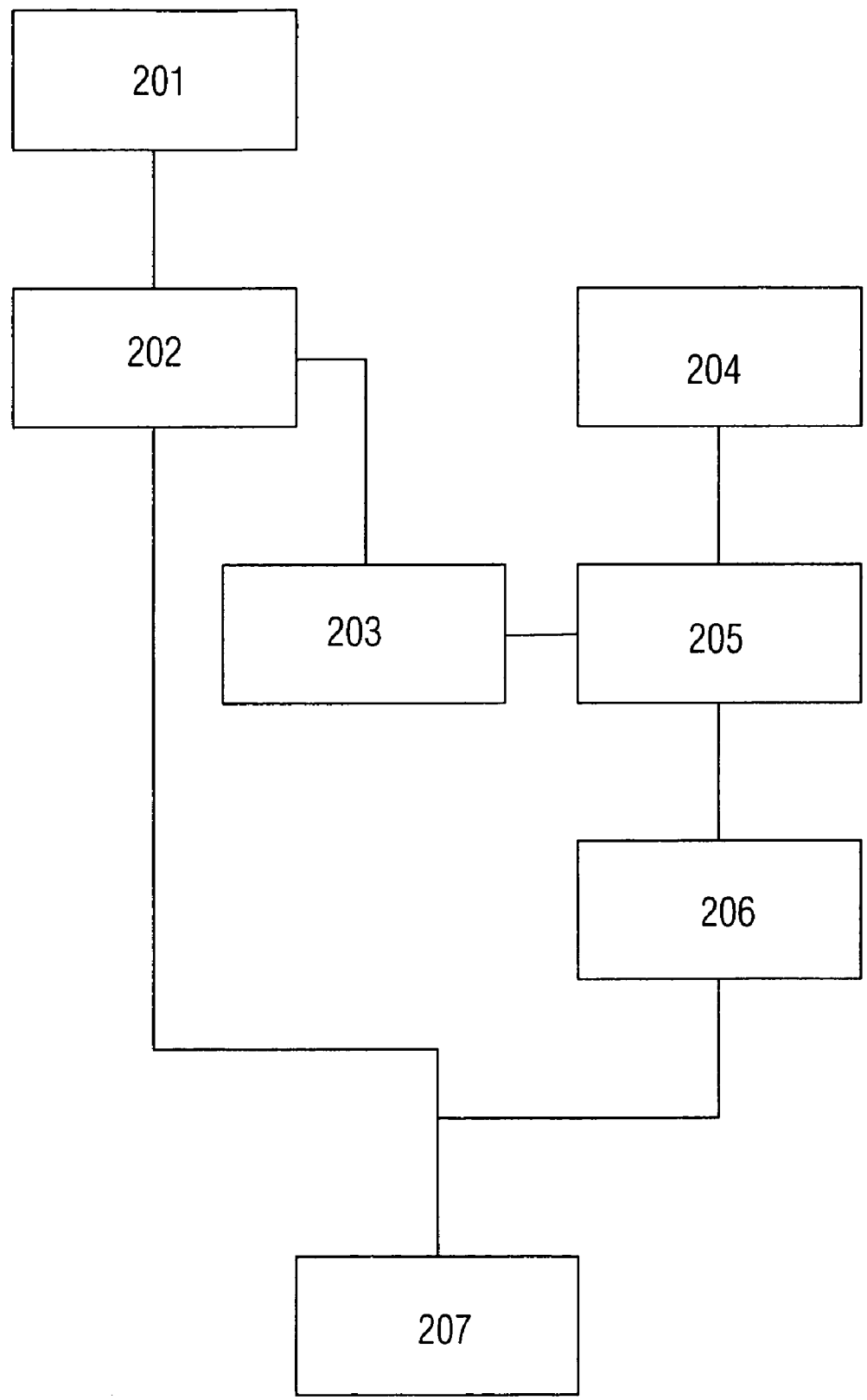
FIG. 4 shows a further method scheme according to an embodiment of the invention.

An example scheme of the method according to at least one embodiment of the invention is illustrated once more in FIG. 4. Here, the measurements are carried out in step 201 with the aid of a wide conical beam, and a reconstruction of the object is undertaken from these measured data in step 202. At the same time, in step 204 the measurements are carried out with the aid of the relatively small conical beam, and in method step 205 the edge beams calculated virtually in step 203 from the reconstructed image are combined to form the relatively small conical beam having the actually measured data, and the entire measuring field thus obtained is reconstructed therefrom in step 206. Subsequently, the two reconstructed images can be combined in step 207, it being possible, for example, to improve the richness of detail in the inner measuring field, or the time resolution of the inner measuring field by comparison with the overall large measuring field.

It goes without saying that the abovenamed features of embodiments of the invention can be used not only in the respectively specified combination, but also in other combinations or on their own without departing from the scope of the invention.

Overall, at least one embodiment of the invention exhibits a method for calculating computed tomography pictures from detector data of a CT that uses at least two radiation sources that generate different conical beams, detector data of a first relatively large conical beam being used to reconstruct a spatial distribution of attenuation values of a scanned object, and the integral attenuation values that are required to supplement the relatively small conical beam being back calculated from these previously reconstructed data, a reconstruction of computed tomography pictures subsequently being carried out with the aid of the back calculated integral attenuation data and the measured integral attenuation data of the relatively small conical beam.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing computed tomography pictures from detector data of a CT that includes at least two radiation sources to generate conical beams, comprising:

scanning an object, using at least two conical beams with fan angles of different sizes and measuring fields of different sizes, in at least one of a circular and spiral fashion, a first conical beam is larger than a second conical beam;

measuring integral attenuation values of the first conical beam;

reconstructing spatial attenuation values of the object by convolution and back projection using the measured integral attenuation values of at least the first conical beam that completely surrounds the object;

scanning the object with the second conical beam, a measuring field of the second conical beam not completely surrounding the object;

measuring integral attenuation values of the second conical beam;

calculating an integral attenuation of virtual rays at least in an area outside of the measuring field of the second conical beam from the reconstructed spatial attenuation values of the area reconstructed using the measured integral attenuation values of the first conical beam;

supplementing the measured integral attenuation values of the second conical beam with the calculated integral attenuation of the virtual rays at an edge of the second conical beam to provide a supplemented data set;

reconstructing the spatial attenuation values of the object, at least in the measuring field of the second conical beam, based on the supplemented data set, to reconstruct the computed tomography pictures, wherein the at least two conical beams used, include different energy spectra, and the difference is considered when calculating the integral attenuation values of the virtual rays.

2. The method as claimed in claim 1, wherein, a focus of the first conical beam and a focus of the second conical beam rotate along a path, the first conical beam scans the object from a position on the path before the second conical beam scans the object from the same position on the path.

3. The method as claimed in claim 1, wherein transitional filtering is undertaken in a transitional area between the calculated integral attenuation values of the virtual rays and measured integral attenuation values of the second conical beam.

4. The method as claimed in claim 1, further comprising:
performing normalization based on the calculated integral attenuation values and measured integral attenuation values of the second conical beam.

5. The method as claimed in claim 1, wherein at least one multirow detector is used in the measuring.

6. The method as claimed in claim 1, wherein a circular scanning takes place and the at least two conical beams are arranged in a common slice layer.

7. The method as claimed in claim 1, wherein a spiral scanning takes place and all the starting points of the at least two conical beams run on a common spiral.

8. The method as claimed in claim 1, wherein a spiral scanning takes place and starting points of the at least two conical beams are arranged in a common slice layer perpendicular to a system axis.

9. The method as claimed in claim 1, wherein different reconstruction methods are carried out based on attenuation data of at least one of the at least two conical beams.

10. The method as claimed in claim 9, wherein a 3D reconstruction method is carried out based on the attenuation data of the second conical beam.

11. The method as claimed in claim 9, wherein a 2D reconstruction method is carried out based on the attenuation data of the first conical beam.

12. The method as claimed in claim 1, wherein a cardio reconstruction is carried out based on attenuation data of the second conical beam.

13. The method as claimed in claim 1, wherein attenuation data of each conical beam are measured on a dedicated detector.

14. The method as claimed in claim 1, wherein attenuation data of the at least two conical beams are measured using a common stationary 360° detector.

15. The method as claimed in claim 2, wherein tomograms are reconstructed from the measured data of the measuring field of the first conical beam, and a three-dimensional image stack is produced, and subsequently this image stack is used to calculate the virtual integral attenuation values for the measurement positions of the measuring field of the second conical beam that is smaller than the measuring field of the first conical beam, the virtual attenuation values being determined for the measuring field of the first conical beam.

16. The method as claimed in claim 2, wherein transitional filtering is undertaken in a transitional area between the calculated integral attenuation values of the virtual rays and measured integral attenuation values of the second conical beam.

17. The method as claimed in claim 2, further comprising:
performing normalization based on the calculated integral attenuation values and measured integral attenuation values of the second conical beam.

18. The method as claimed in claim 9, wherein a voxelwise reconstruction is carried out based on the attenuation data of the second conical beam.

19. The method as claimed in claim 1, wherein a cardio reconstruction, making use of simultaneously determined ECG data, is carried out based on the attenuation data of the second conical beam.

20. A computer-readable medium storing executable instructions which when executed by a computed tomography system causes the computed tomography system to perform a method comprising:
scanning an object, using at least two conical beams with fan angles of different sizes and measuring fields of different sizes, in at least one of a circular and spiral fashion, a first conical beam is larger than a second conical beam;
measuring integral attenuation values of the first conical beam;
reconstructing spatial attenuation values of the object by convolution and back projection using the measured integral attenuation values of at least the first conical beam that completely surrounds the object;
scanning the object with the second conical beam, a measuring field of the second conical beam not completely surrounding the object;
measuring integral attenuation values of the second conical beam;
calculating an integral attenuation of virtual rays at least in an area outside of the measuring field of the second conical beam from the spatial attenuation values of the area reconstructed using the measured integral attenuation values of the first conical beam;
supplementing the measured integral attenuation values of the second conical beam with the calculated integral attenuation values of the virtual rays at an edge of the second conical beam to provide a supplemented data set;
reconstructing the spatial attenuation values of the object, at least in the measuring field of the second conical beam, based on the supplemented data set, to reconstruct the computed tomography pictures, wherein
the at least two conical beams used, include different energy spectra, and the difference is considered when calculating the integral attenuation values of the virtual rays.

21. A computed tomography system, comprising:
at least two radiation sources to scan an object with at least two conical beams with fan angles of different sizes and measuring fields of different sizes, in at least one of a circular and spiral fashion, a first conical beam is larger than a second conical beam;
means for measuring integral attenuation values of the at least two conical beams;
means for reconstructing spatial attenuation values of the object by convolution and back projection using the measured integral attenuation values of at least the first conical beam that completely surrounds the object;
means for scanning the object with the second conical beam;
means for calculating an integral attenuation of virtual rays at least in an area outside of the measuring field of the second conical beam from the reconstructed spatial attenuation values of the area reconstructed using the measured integral attenuation values of the first conical beam;
means for supplementing the measured integral attenuation values of the second conical beam with the calculated integral attenuation of the virtual rays at an edge of the second conical beam to provide a supplemented data set; and
means for reconstructing the spatial attenuation values of the object, at least in the measuring field of the second conical beam, based on the supplemented data set, wherein
the at least two conical beams used, include different energy spectra, and the difference is considered when calculating the integral attenuation values of the virtual rays.

* * * * *